United States Patent
Fukumoto et al.

(10) Patent No.: US 8,324,597 B2
(45) Date of Patent: Dec. 4, 2012

(54) LIGHT DETECTION DEVICE

(75) Inventors: Atsushi Fukumoto, Kanagawa (JP); Isao Ichimura, Tokyo (JP); Shinichi Kai, Tokyo (JP); Toshio Watanabe, Kanagawa (JP); Yuji Segawa, Tokyo (JP)

(73) Assignee: Sony Corporation, Tokyo (JP)

( * ) Notice: Subject to any disclaimer, the term of this patent is extended or adjusted under 35 U.S.C. 154(b) by 219 days.

(21) Appl. No.: 12/848,340

(22) Filed: Aug. 2, 2010

(65) Prior Publication Data

US 2011/0036992 A1    Feb. 17, 2011

(30) Foreign Application Priority Data

Aug. 12, 2009  (JP) ................ P2009-187525
Nov. 6, 2009   (JP) ................ P2009-254508

(51) Int. Cl.
 *H05B 33/00*  (2006.01)
(52) U.S. Cl. ............................................. 250/483.1
(58) Field of Classification Search ........... 250/483.1, 250/458.1, 459.1
See application file for complete search history.

(56) References Cited

U.S. PATENT DOCUMENTS

| 6,437,345 B1 * | 8/2002 | Bruno-Raimondi et al. .......... 250/458.1 |
| 7,170,597 B1 * | 1/2007 | Rushbrooke et al. ......... 356/317 |

FOREIGN PATENT DOCUMENTS

| JP | 2007-139744 | 6/2007 |
| JP | 2007-187582 | 7/2007 |
| JP | 2008-015770 | 1/2008 |
| JP | 2008-017779 | 1/2008 |

* cited by examiner

*Primary Examiner* — Kiho Kim
(74) *Attorney, Agent, or Firm* — K&L Gates LLP

(57) ABSTRACT

Disclosed herein is a light detection device including, at least, a substrate provided with a plurality of detection regions where to perform detection of fluorescent light emitted from the inside of a sample upon irradiation of the sample with light, a light irradiation section operable to perform the irradiation with light, an optical control section configured to irradiate the detection regions with the light radiated from the light irradiation section, and a light detection section operable to detect the fluorescent light.

10 Claims, 13 Drawing Sheets

LIGHT DETECTION DEVICE

CROSS REFERENCES TO RELATED APPLICATIONS

The present application claims priority to Japanese Priority Patent Application JP 2009-187525 filed in the Japan Patent Office on Aug. 12, 2009 and JP 2009-254508 filed in the Japan Patent Office on Nov. 6, 2009, the entire content of which is hereby incorporated by reference.

BACKGROUND

The present application relates to a light detection device. More particularly, the present application relates to a light detection device for use in gene expression analysis, infectious-disease tests, gene analysis (e.g., SNP analysis), protein analysis, cell analysis or the like.

In recent years, research and development relating to gene analysis, protein analysis, cell analysis and the like have been widely conducted in various fields such as medical fields as well as the fields of drug design, clinical tests, foods, agriculture, engineerings, forensic medicine, criminal identification, etc. Especially, development and putting into practical use of the lab-on-chip technology have recently been under way, in which various reactions for detection and/or analysis of nucleic acids, proteins, cells, etc. are carried out in micro-scale channels or wells provided on a chip. The lab-on-chip technology has been drawing attention as a technique for easy measurement of biomolecules and the like.

In such a lab-on-chip technology for performing reactions in micro-scale channels or wells provided on a chip, there is a keen request for development of a device with which various analyses can be carried out in actual scenes (e.g., medical sites). Thus, how to realize the downsizing of device is an inevitable problem to be solved. Therefore, in order to achieve efficient detection and/or analysis in a compact device, it may be necessary to make various ingenuities as to the chips and devices used, the detecting and/or analyzing methods adopted, and the like.

For example, Japanese Patent Laid-open No. 2008-151770 proposes a microchannel chip with which reductions in size and manufacturing cost can be achieved. In the microchannel chip, specifically, a reagent in mixture with a heat-soluble binder is carried at predetermined positions in the microchannels. Then, the heat-soluble binder begins to be dissolved at the predetermined positions by a temperature rise from the temperature at which a specimen is introduced, whereby the dissolving treatment and the mixing treatment can be carried out efficiently. Further, the subsequent reaction treatment and analyzing treatment can be carried out at the same positions, so that the number of treatment positions on the microchannels can be reduced, leading to the reductions in size and cost.

Japanese Patent Laid-open No. 2007-139744 proposes a fluorescent polarimetric method by which a sample can be analyzed while using the sample in an amount of about 1/100 times that required in the methods according to the related art. The fluorescent polarimetric method, specifically, includes (1) a step of preparing a fluorescent probe molecule and a biomolecule, (2) a step of pouring the fluorescent probe molecule and the biomolecule into a microchannel of a lab-on-a-chip system so as to form a complex, (3) a step of irradiating the complex with polarized light and measuring the resulting fluorescent polarized light, and (4) quantifying the fluorescent polarized light and determining the degree of fluorescent polarization.

Japanese Patent Laid-open No. 2008-17779 proposes a lab-on-chip system by which nucleic acid replication, synthesis, reaction, detection, and the like can be carried out on a single substrate. Specifically, the substrate is provided thereon with a nucleic acid preparing section having a first electrode, a sample inflow section for inflow of a sample fluid into the nucleic acid preparing section, a reaction section having a second electrode which communicates with the nucleic acid preparing section though a channel, a medicinal liquid inflow section for inflow of a medicinal liquid into the reaction section, an outflow section for outflow of a fluid from the reaction section, a control circuit interconnecting the first and second electrodes, and a detection circuit connected with the second electrode.

Japanese Patent Laid-open No. 2007-187582 proposes a biochip which has detection electrodes including a working electrode, a reference electrode and a counter electrode, and a thin film transistor. With the biochip having these components, it is possible to realize a biosensing device which is small in weight, thickness, length, etc., high in performance, and low in cost. Further, the biochip can be mounted to and dismounted from a biosensor which has an ink jet head unit.

SUMMARY

In general, the detection of a substance present in a sample is carried out by detection of light such as fluorescent light emitted from the inside of the sample upon irradiation with light of the sample introduced into a lab-on-chip system. In many cases, the irradiation of the sample with light and the detection of light are normally conducted in a plurality of locations in the chip. In order to conduct the irradiation with light in a plurality of locations, it may be necessary to provide a plurality of light irradiation means, which inevitably leads to an enlarged device size and an increased energy consumption.

Meanwhile, irradiation of a plurality of locations in a chip with light can be performed by scanning single light irradiation means on the chip. In this case, means for scanning the light irradiation means has to be provided separately, which also inevitably leads to an enlarged device size and an increased energy consumption.

Thus, there is a need for a technology by which irradiation with light can be performed in a plurality of locations on a chip and, yet, reductions in device size and in energy consumption can be realized.

In order to solve the above-mentioned problem, the present inventors made intensive and extensive researches. As a result of their researches, by paying attention to the method for controlling light radiated from light irradiation means, the inventors have succeeded in reducing device size and energy consumption in a device in which irradiation with light can be performed in a plurality of locations on a chip.

According to an embodiment, there is provided a light detection device including, at least:

a substrate provided with a plurality of detection regions where to perform detection of fluorescent light emitted from the inside of a sample upon irradiation of the sample with light;

light irradiation means operable to perform the irradiation with light;

optical control means for irradiating the detection regions with the light radiated from the light irradiation means; and light detection means operable to detect the fluorescent light.

In the light detection device, the direction of irradiation with light from the light irradiation means is not particularly limited. For instance, the irradiation with light may be conducted from a lateral side of the substrate. In addition, the light radiated from the light irradiation means can be optically controlled so as to enable irradiation of the plurality of detection regions with the light, by use of a plurality of lenses or mirrors arranged on an optical path of the light radiated from the light irradiation means in the manner of corresponding to the plurality of detection regions.

Besides, the light radiated from the light irradiation means can be optically controlled so as to enable irradiation of the plurality of detection regions with the light, also by performing the irradiation with the light from a lateral side of the substrate and using a light guide plate.

In addition, in the light detection device according to an embodiment, for example, a beam splitting element may be arranged on an optical path of the light radiated from the light irradiation means. By use of the beam splitting means, also, the light radiated from the light irradiation means can be optically controlled so as to enable irradiation of the plurality of detection regions with the light.

The detection region in the light detection device according to an embodiment is not particularly limited in specific configuration, insofar as the detection region permits detection of fluorescent light emitted from the inside of the sample upon irradiation of the sample with light. For example, the detection regions may be provided in a plurality of wells or channels.

According to embodiments, the light radiated from the light irradiation means can be optically controlled so as to enable irradiation of the plurality of detection means with the light. Therefore, the plurality of detection regions can be irradiated with light assuredly, notwithstanding the number of the light irradiation means is set smaller than the number of the detection regions. As a result, a reduction in overall device size and a reduction in energy consumption can be realized.

Additional features and advantages are described herein, and will be apparent from the following Detailed Description and the figures.

DETAILED DESCRIPTION

Figure 1:
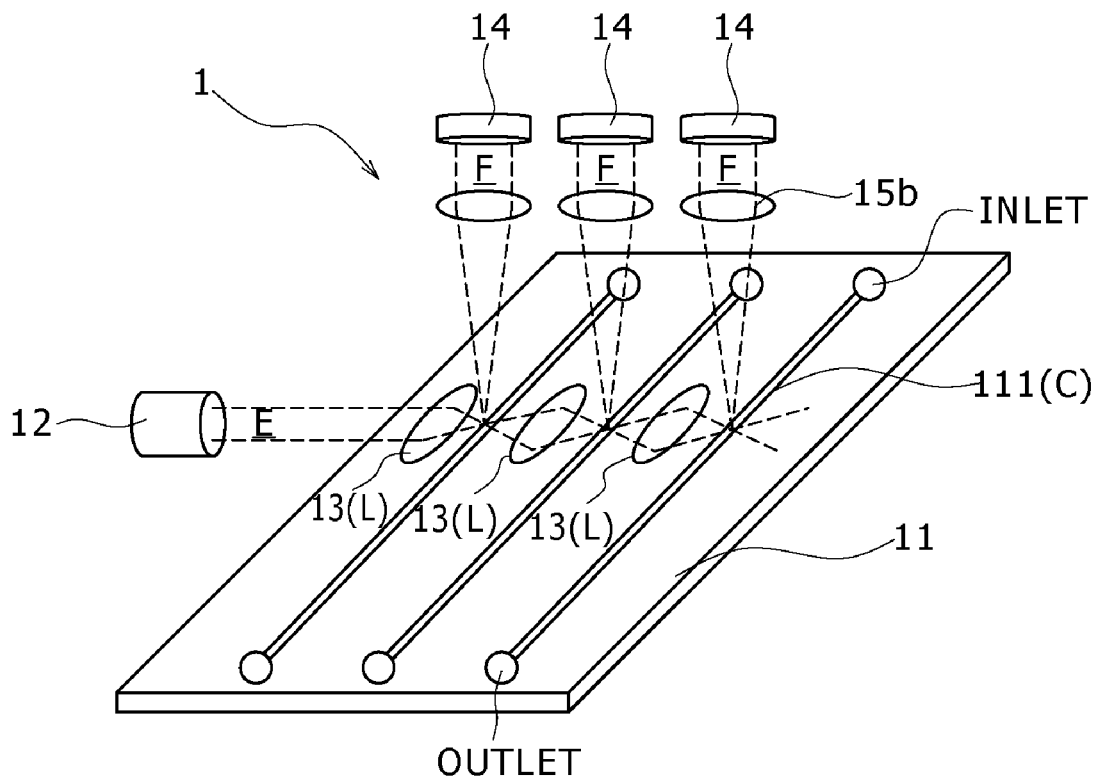
FIG. 1 is a schematic perspective view of a first embodiment of a light detection device.

The present application will be described below referring to the drawings according to an embodiment. The description will be made in the following order:

1. Light detection device 1
   (1) Substrate 11
   (2) Light irradiation means 12
   (3) Optical control means 13
      (a) Lens L
      (b) Mirror M
      (c) Light guide plate G
      (d) Beam splitting element B
      (e) Method of adjusting the spot positions in the case where light guide plate G or beam splitting element B is used
   (4) Light detection means 14
   (5) Condenser lens 15$a$, 15$b$
   (6) Optical filter 16$a$, 16$b$
   (7) Aperture member 17$a$, 17$b$, partition wall <1. Light Detection Device 1>

FIG. 1 is a sectional view schematically showing a first embodiment of a light detection device 1 according to embodiments. The light detection device 1 according to embodiments is a device which includes, at least (1) a substrate 11, (2) light irradiation means 12, (3) optical control means 13, and (4) light detection means 14. If necessary, the light detection device 1 may further include (5) condenser lens 15a, 15b, (6) optical filter 16a, 16b, and (7) aperture member 17a, 17b, partition wall and the like. Now, these components will be described in detail below.

(1) Substrate 11

The substrate 11 is provided with a plurality of detection regions 111. The detection regions 111 are each a region in which a sample as an object of detection is present and where detection of fluorescent light F emitted from the inside of the sample upon irradiation of the sample with light (excitation light E) is carried out.

The detection region 111 in the light detection device 1 according to an embodiment is not particularly limited in specific configuration, insofar as the detection region permits detection of fluorescent light F emitted from the inside of a sample upon irradiation of the sample with light (excitation light E). For example, as in a first embodiment shown in FIG. 1, the detection regions 111 may be provided in channels C. Incidentally, while one detection region 111 is provided in one channel C in the first embodiment illustrated in FIG. 1, this configuration is not limitative, and, as will be described later, a plurality of detection regions 11 may be provided in one channel C.

Figure 2:
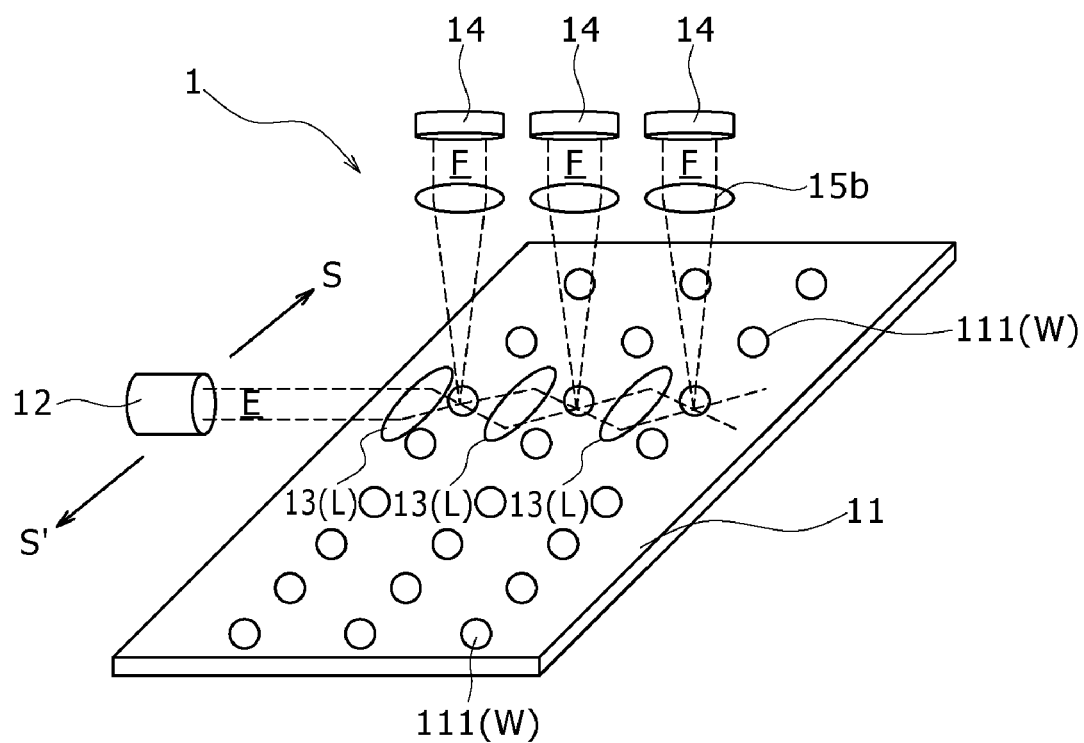
FIG. 2 is a schematic perspective view of a second embodiment of the light detection device.
Figure 3:
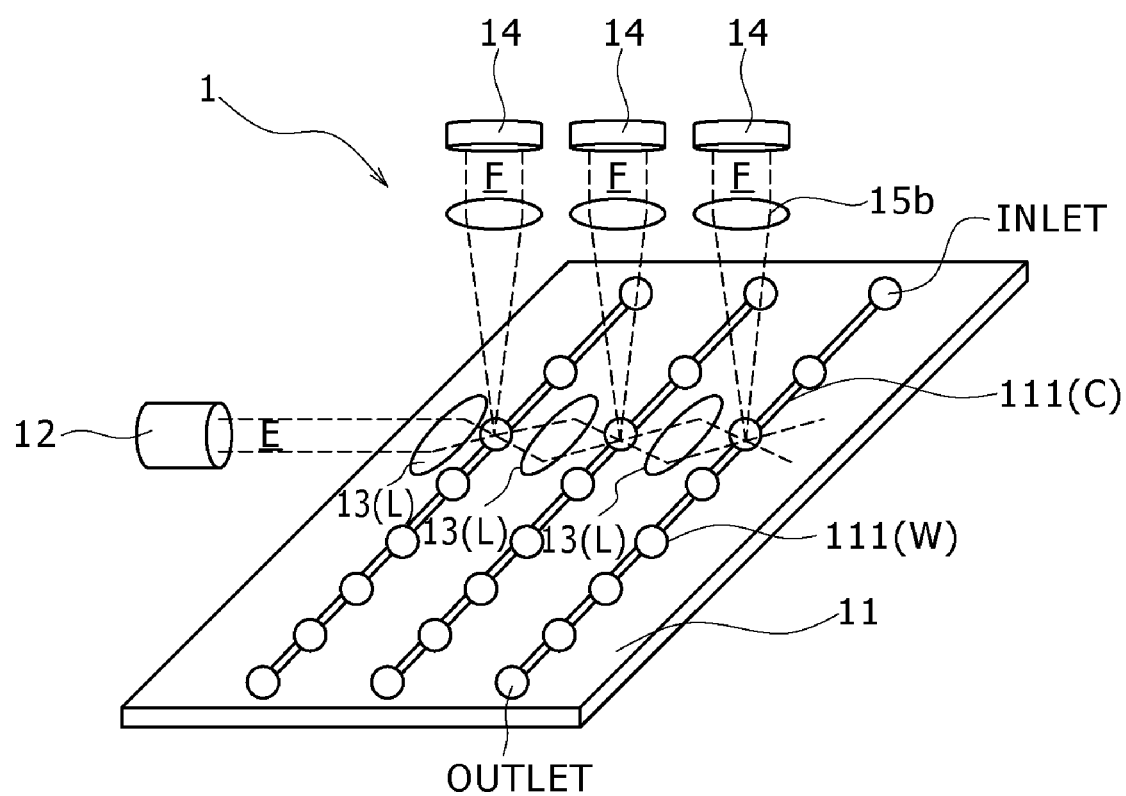
FIG. 3 is a schematic perspective view of a third embodiment of the light detection device.

In addition, as in a second embodiment shown in FIG. 2, detection regions 111 may also be provided in wells W. Further, as in a third embodiment shown in FIG. 3, a configuration may be adopted in which the substrate 11 is provided therein with wells W and channels C in combination, and a plurality of detection regions 111 are provided in the wells W and in the channels C.

Where the detection regions 111 are provided in the channels C, the width, depth and cross-sectional shape of the channels C are not particularly limited, and can be designed freely. For example, microchannels of not more than 1 mm in channel width can also be used in the light detection chip 1 according to an embodiment.

The detection region 111 can be used not only for detection of florescent light but also as reaction sites where, for example, amplification of nucleic acid, hybridization, interaction between materials such as nucleic acids, proteins, cells, etc. or the like proceeds. In addition, where the detection regions 111 are provided in the channels C as in the first embodiment shown in FIG. 1, a mode may be adopted in which each reaction is allowed to proceed while the sample is moved in the channel C, and detection of fluorescent light is conducted at the time when the sample reaches a predetermined position. Further, where the substrate 11 is provided with wells W and channels C in combination as in a third embodiment shown in FIG. 3, a mode may be adopted in which each reaction is allowed to proceed while the sample is moved in the channel C and detection of fluorescent light is conducted at the time when the sample reaches the well W, or, alternatively, a mode may be adopted in which each reaction is allowed to proceed in the well W and detection of fluorescent light is conducted while the sample is moved in the channel C.

The material for forming the substrate 11 in the light detection device 1 according to an embodiment is not particularly limited, and can be freely selected from those materials which can normally be used for light detection chips such as bioassay chips. In an embodiment, particularly, since the system is used for detection of light, the substrate 11 is preferably formed from a light-transmitting material such as plastic resins such as polycarbonate, polyolefin resins, acrylic resins, etc., silicone resins such as PDMS (polydimethylsiloxane), etc., glasses, and so on.

(2) Light Irradiation Means 12

Light irradiation means 12 is a means for irradiating a sample with excitation light E. The light detection device 1 according to an embodiment has optical control means 13 to be described later, so that a plurality of detection regions 111 can be irradiated with light from single light irradiation means 12. Therefore, even where a plurality of detection regions 111 must be irradiated with light, the number of the light irradiation means 12 can be reduced, as compared with light detection devices according to the related art. This contributes to reductions in device size and energy consumption.

In the light detection device 1 according to an embodiment, the method of specifically laying out the light irradiation means 12 is not particularly limited, and the light irradiation means 12 can be arranged freely, insofar as irradiation of samples with light is possible. For example, even where only one light irradiation means 12 is provided for one substrate 11 as in the first to third embodiments shown in FIGS. 1 to 3, irradiation of a plurality of detection regions 111 with light is possible because the light detection device 1 according to an embodiment is provided with the optical control means 13 to be described later. In this case, for example, by scanning the light irradiation means 12 in a direction perpendicular to the optical path for the excitation light E used for irradiation (see reference symbols S and S' in FIG. 2) as in the second embodiment shown in FIG. 2, all the detection regions 111 provided on the substrate 11 can be irradiated with light assuredly.

Figure 4:
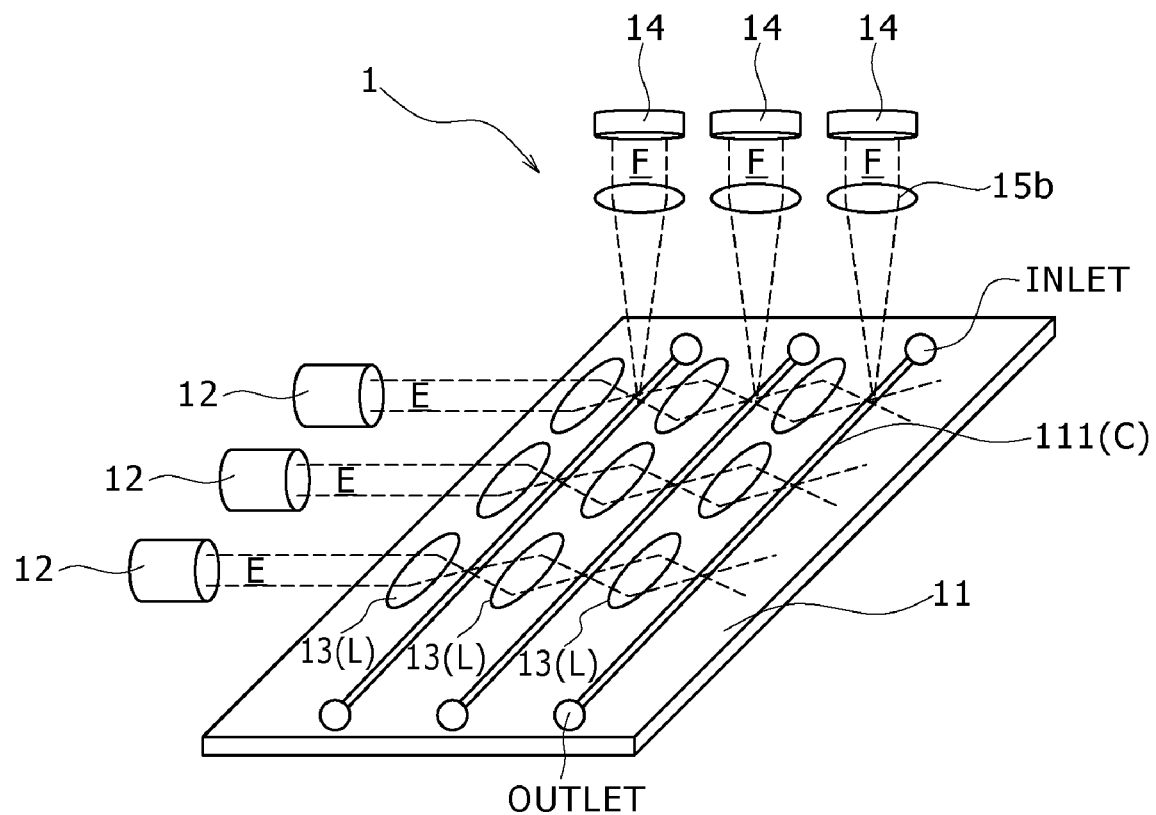
FIG. 4 is a schematic perspective view of a fourth embodiment of the light detection device.

Besides, for example, one substrate 11 can be provided with a plurality of light irradiation means 12, as in a fourth embodiment shown in FIG. 4. With the plurality of light irradiation means 12 thus arranged, it is possible, for example, to irradiate each detection region 111 with excitation lights E of different wavelengths, thereby performing different detections simultaneously.

In the light detection device 1 according to an embodiment, the direction of irradiation with light from the light irradiation means 12 may be freely set according to the function of the optical control means 13 to be described later. For example, where lenses, mirrors, a light guide plate or the like is used as the optical control means 13, irradiation with light may be conducted from a lateral side of the substrate 11 (see FIGS. 1 to 8). On the other hand, where for example a beam splitting element or the like is used as the optical control means 13, irradiation with light may be conducted from above the substrate 11 or from below the substrate 11 (see FIGS. 10, 11, 18, and 21).

The method of irradiation with light (the method of radiating light) which is applicable to the light irradiation means 12 in the light detection device 1 according to an embodiment is not particularly limited, and one or more of known light irradiation methods (light-radiating methods) can be selected for use here. For example, one or more of light irradiation methods employing LED (light emitting diode), semiconductor laser, EL illumination or the like can be used.

Where a plurality of light irradiation means 12 are arranged correspondingly to the substrate 11, the light irradiation means 12 may be turned on simultaneously and the detections may be conducted simultaneously by use of the light detection means 14 to be described later, whereby signal pickup time can be shortened. Or, alternatively, the light irradiation means 12 may be turned on sequentially at a high sequential switching speed, whereby noises from the adjacent light irradiation means 12 can be suppressed.

(3) Optical Control Means 13

The optical control means 13 is a means for performing an optical control for irradiating a plurality of detection regions 111 with light (excitation light E) radiated from the light irradiation means 12. Since the optical control means 13 is provided, in the light detection device 1 according to an embodiment, it is possible to irradiate the plurality of detection regions 111 with light radiated from one light irradiation means 12. Therefore, even where a plurality of detection regions 111 must be irradiated with light, the number of the light irradiation means 12 can be reduced, as compared with light detection devices according to the related art. This contributes to reductions in device size and in energy consumption. Now, specific configurations of optical control means 13 which can be used in the light detection device 1 according to an embodiment will be described in detail below, by showing specific examples thereof.

(a) Lens L

In the light detection device 1 according to an embodiment, lenses L may be used as the optical control means 13, as in the first to fourth embodiments shown in FIGS. 1 to 4. For instance, a plurality of lenses L may be inserted in the optical path of the light (excitation light E) radiated from the light irradiation means 12 in the manner of corresponding to the detection regions 111. With such a configuration, condensation of the excitation light E toward the detection region 111 and re-amplification of the condensed excitation light E can be repeated on the optical path of the excitation light E. With a plurality of lenses L thus inserted in the optical path of the excitation light E, all the plurality of detection regions 111 can be sufficiently irradiated with the excitation light E, without a reduction in the quantity of the excitation light E radiated from the light irradiation means 12.

Figure 5:
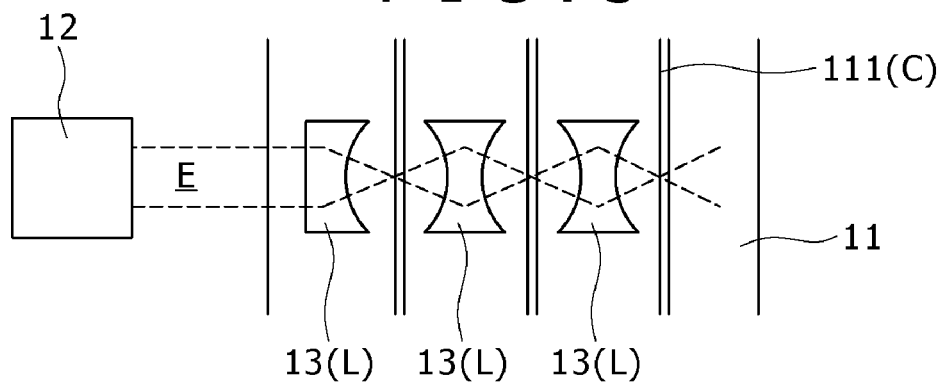
FIG. 5 is a schematic top plan view, as viewed from above a substrate 11, of only an excitation system in a fifth embodiment of the light detection device.

In the light detection device 1 according to an embodiment, the kind of the lenses L which can be used as the optical control means 13 is not particularly limited, and those lenses which can be used in light detection devices can be freely selected for use here. For instance, not only convex lenses used in the first to fourth embodiments shown in FIGS. 1 to 4 but also concave lenses as in a fifth embodiment shown in FIG. 5 can be used. Incidentally, FIG. 5 is a schematic top plan view, as viewed from above a substrate 11, of only an excitation system in the fifth embodiment of the light detection device 1 according to embodiments.

(b) Mirror M

Figure 6:
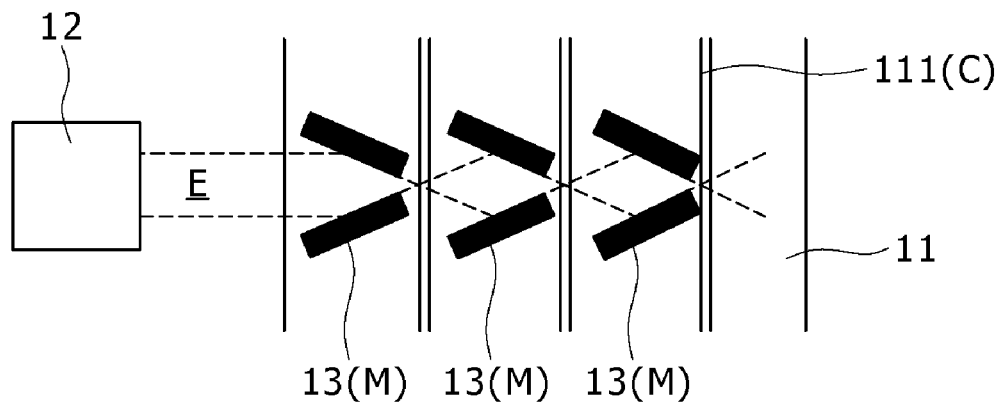
FIG. 6 is a schematic top plan view, as viewed from above a substrate 11, of only an excitation system in a sixth embodiment of the light detection device.

FIG. 6 is a schematic top plan view, as viewed from above a substrate 11, of only an excitation system in a sixth embodiment of the light detection device 1 according to an embodiment. In the light detection device 1 according to embodiments, mirrors M can be used as the optical control means 13, as in this embodiment. For example, a plurality of mirrors M may be inserted in the optical path of the light (excitation light E) radiated from the light irradiation means 12, whereby the excitation light E can be condensed toward the detection regions 111 on the optical path of the excitation light E. With a plurality of mirrors M thus inserted in the optical path of the excitation light E, all the plurality of detection regions 111 can be sufficiently irradiated with the excitation light E, without a reduction in the quantity of the excitation light E radiated from the light irradiation means 12.

(c) Light Guide Plate G

Figure 7:
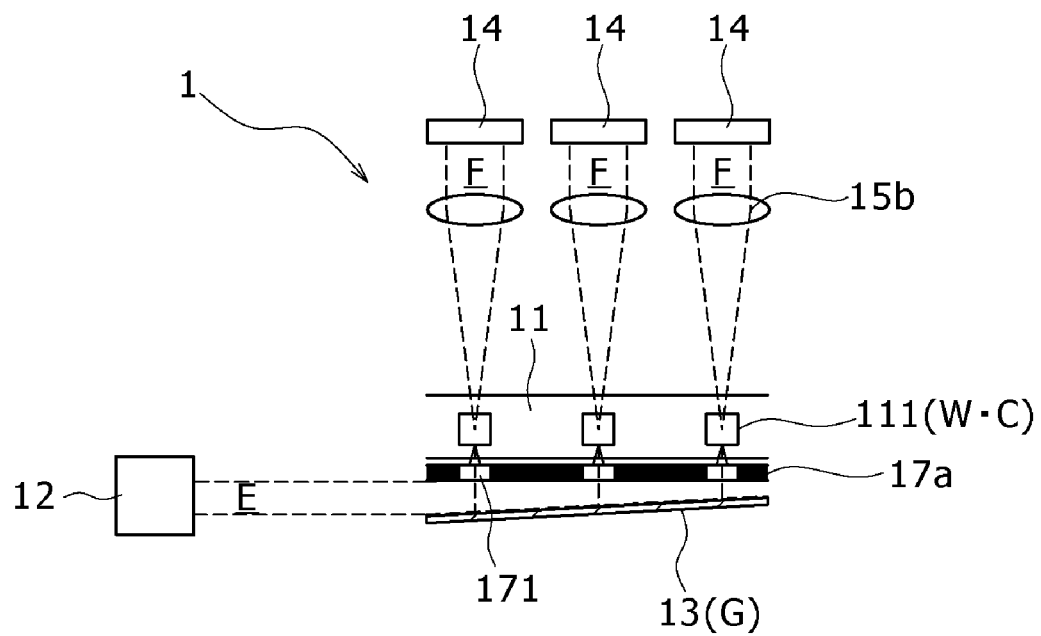
FIG. 7 is a schematic side sectional view, as viewed from a lateral side of a substrate 11, of the seventh embodiment of the light detection device.

FIG. 7 is a schematic side sectional view, as viewed from a lateral side of a substrate 11, of a seventh embodiment of the light detection device 1 according to an embodiment. In the light detection device 1 according to embodiments, a light guide plate G can be used as the optical control means 13, as in this embodiment. For instance, the light guide plate G may be disposed on the optical path of the light (excitation light E) radiated from the light irradiation means 12, and an aperture member 17a provided with apertures 171 correspondingly to the detection regions 111 may be interposed between the light guide plate G and the substrate 11, whereby the plurality of detection regions 111 can be irradiated with the excitation light E.

Figure 8:
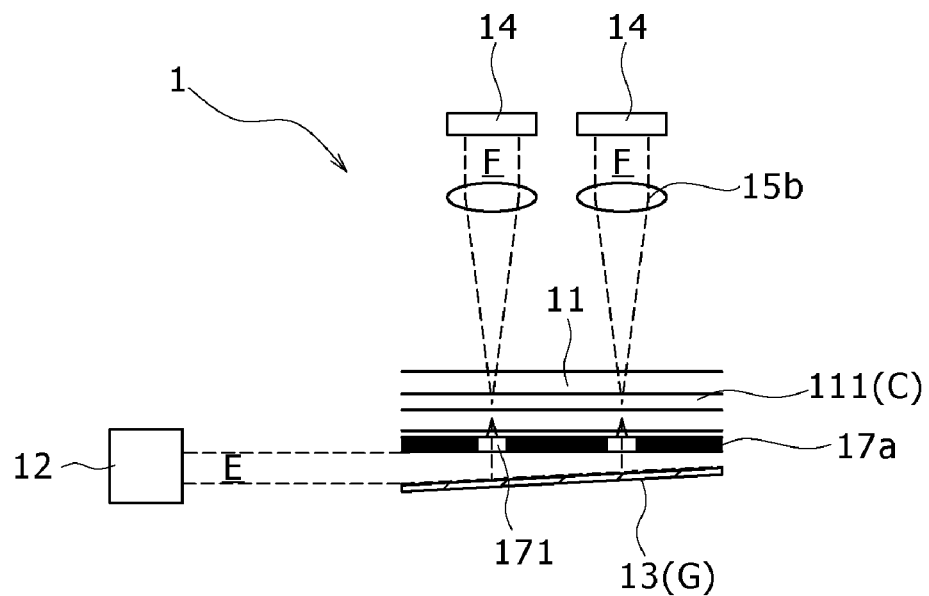
FIG. 8 is a schematic side sectional view, as viewed from a lateral side of a substrate 11, of an eighth embodiment of the light detection device.
Figure 9:
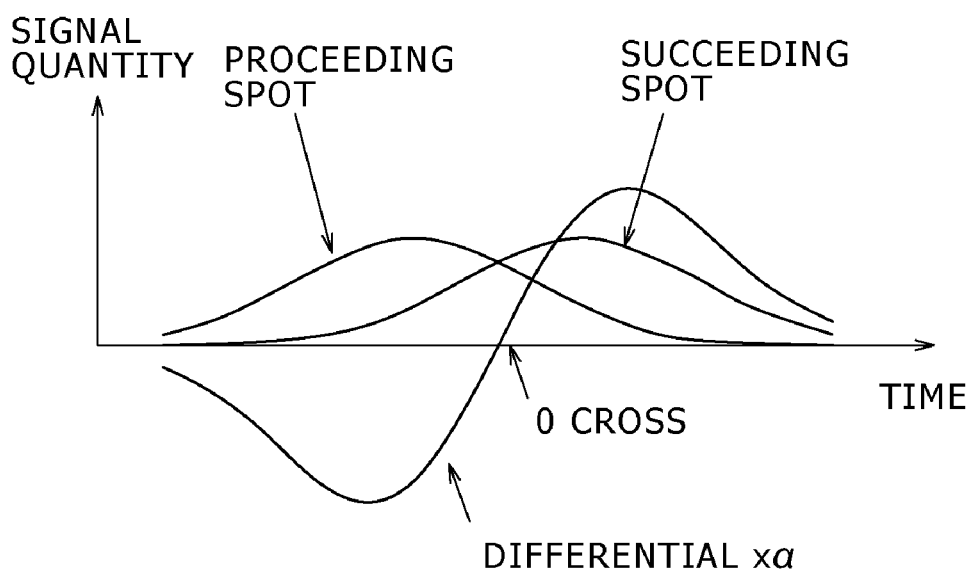
FIG. 9 is a graph substituted for drawing, showing an example of the result of detection by detection means in the light detection device.

Incidentally, while the irradiation with light by use of the light guide plate G can be performed at one location in one channel C as in the seventh embodiment shown in FIG. 7, the irradiation with light can also be conducted at a plurality of locations in one channel C as in an eighth embodiment shown in FIG. 8, for example. Where a plurality of locations relative to the flow direction in the channel C are thus irradiated with light, for example, a result as shown in FIG. 9 can be obtained by the light detection means 14 to be described later. In this case, by differentiating the signal quantity relevant to a proceeding spot and that relevant to a succeeding spot, in-phase noises are canceled, so that the SN of a differential signal is enhanced. Besides, by detecting a zero crossing (zero cross) of the differential signal, the accurate passage time of a substance flowing in the channel C can be measured.

(d) Beam Splitting Element B

Figure 10:
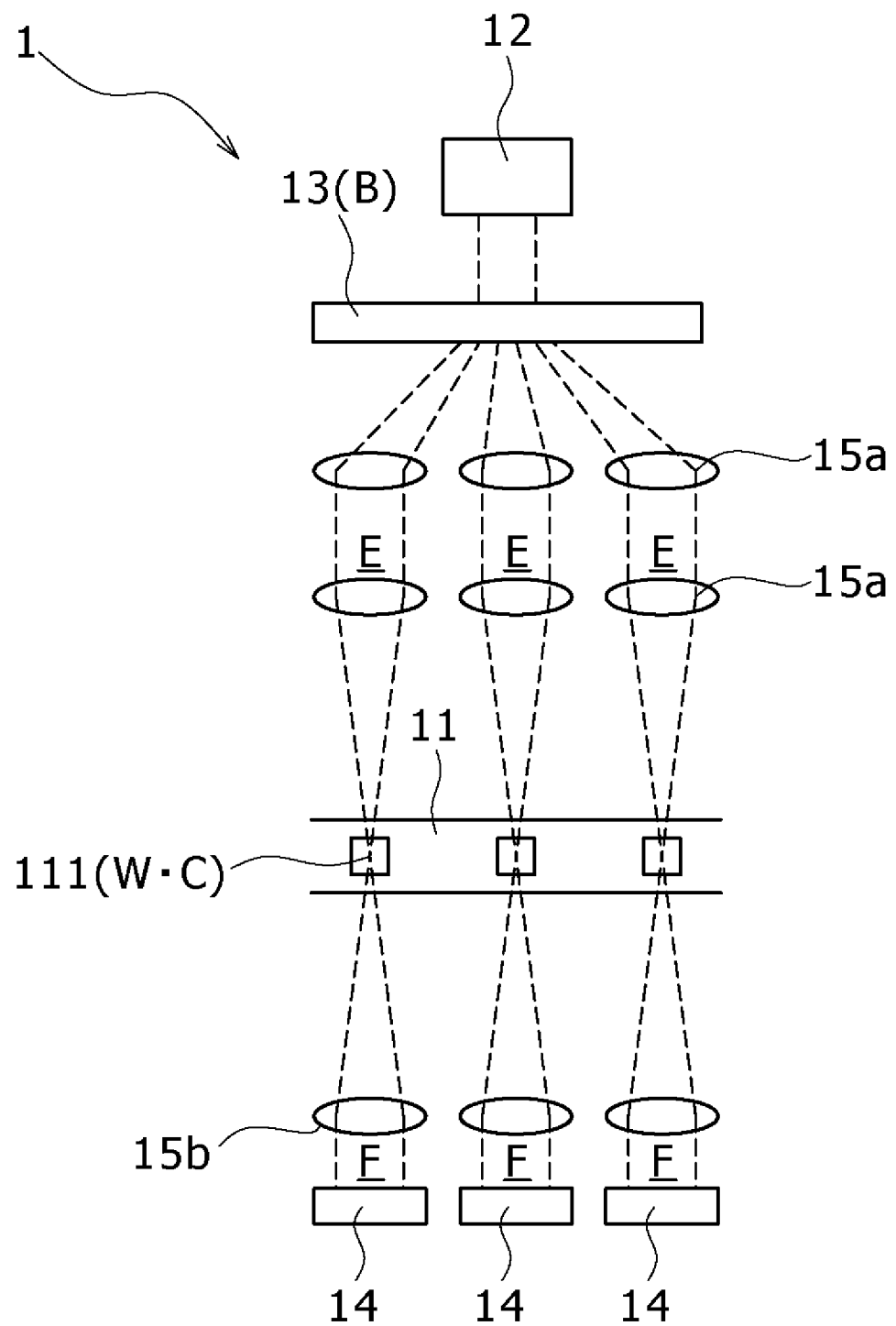
FIG. 10 is a schematic side sectional view, as viewed from a lateral side of a substrate, of a ninth embodiment of the light detection device.

FIG. 10 is a schematic side sectional view, as viewed from a lateral side of a substrate 11, of a ninth embodiment of the light detection device 1 according to an embodiment. In the light detection device 1 according to embodiments, a beam splitting element B may be used as the optical control means 13, as in this embodiment. For example, the beam splitting element B may be disposed on the optical path of the light (excitation light E) radiated from the light irradiation means 12, whereby the excitation light E emitted from the light irradiation means 12 can be split into a plurality of beams (luminous fluxes), and a plurality of detection regions 111 can be simultaneously irradiated with the split beams of the excitation light E.

In the light detection device 1 according to embodiments, the kind of the beam splitting element B which can be used as the optical control means 13 is not particularly limited, and beam splitting elements which can be used in light detection devices can be freely selected for use here. For instance, a grating, a prism, and a lens array as in a tenth embodiment shown in FIG. 11 can be used.

Figure 12:
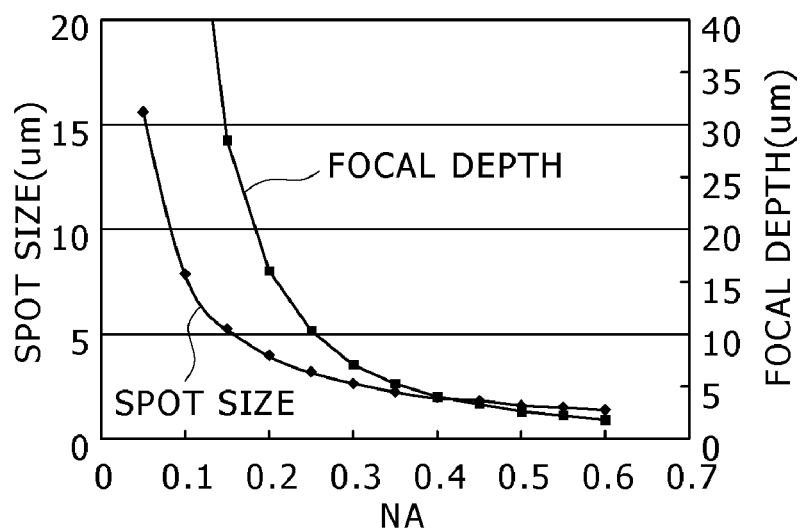
FIG. 12 is a graph substituted for drawing, showing the relationships between numerical aperture NA and spot size as well as focal depth in the case of a wavelength of 640 nm.

In the case where a lens array is used, when a channel is irradiated with excitation light by use of a light source with a wavelength $\lambda$ and an objective lens with a numerical aperture NA, the size of the spot formed on the channel is $1.22\lambda/NA$. Besides, the focal depth of the spot is $\lambda/NA^2$. The relationships between the numerical aperture NA and the spot size as well as the focal depth in the case of a wavelength of 640 nm are shown in FIG. 12.

Where the width of the channels C used is assumed to be 10 to 20 μm, the size of the spot formed on the channel C is desirably about 2 to 8 μm. In addition, where the depth of the channels C is assumed to be 10 to 20 μm, the focal depth is desirably not less than 10 μm, taking the position control error in the direction of the optical axis of the irradiation optical system into account. Based on these conditions, the numerical aperture NA of the lenses used for irradiation with light is desirably in the range of 0.1 to 0.25. The numerical aperture of the objective lens used here may not necessarily be in this range of numerical aperture. Where lenses with a larger numerical aperture are used, it is possible, by reducing the sectional size of the irradiation light or inserting some optical element, to realize the spot size and the focal depth in the above-mentioned respective ranges.

Figure 11:
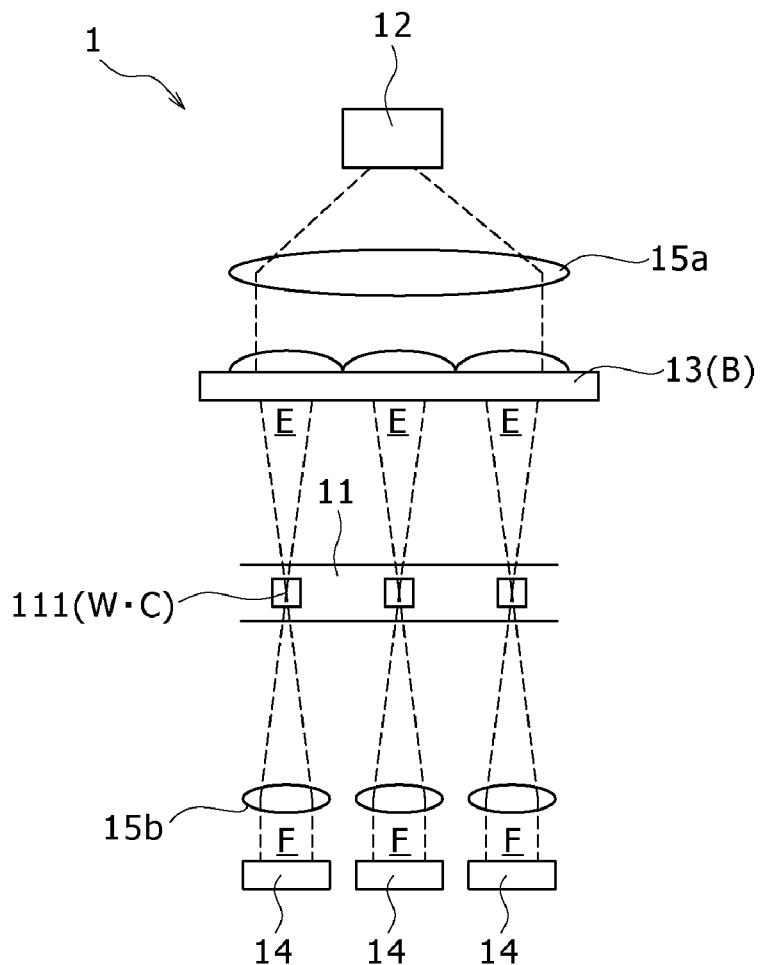
FIG. 11 is a schematic side sectional view, as viewed from a lateral side of a substrate, of a tenth embodiment of the light detection device.
Figure 13:
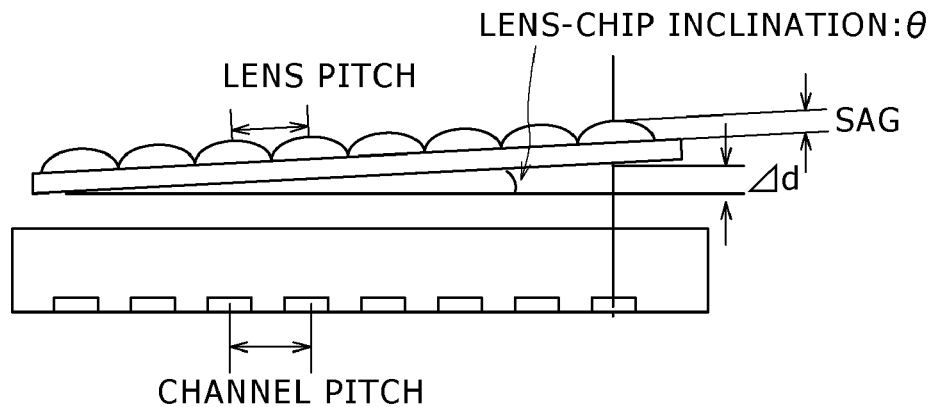
FIG. 13 is schematic illustration of an example of the inclination generated between a channel chip and a lens array.

In the case where a lens array composed of the same number of lenses as the number of channels C is used for a chip having a plurality of channels C as in the tenth embodiment shown in FIG. 11 and where all the channels C are excited simultaneously, an inclination may be generated between the channel chip and the lens array, as shown in FIG. 13.

For example, where a chip having N channels C and a lens array form an angle θ therebetween, the difference Δd in focal position in the optical axis direction between the left-end lens and the right-end lens is represented by the following formula (1). Besides, for uniform excitation of the channels C, the value of Δd (together with the spot position control error a in the optical axis direction) should be within the focal depth, as shown in the following formula (2).

[Mathematical 1]

$$\Delta d = p \times (N-1) \times \tan \theta \quad (1)$$

[Mathematical 2]

$$\Delta d + \alpha \leq \text{focal depth}(\lambda/NA^2) \quad (2)$$

Figure 14:
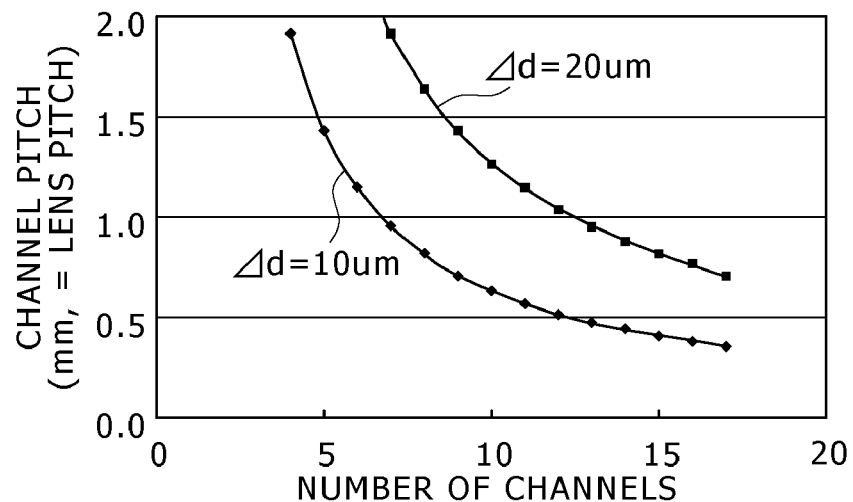
FIG. 14 is a graph substituted for drawing, showing the relationship between the number of channels, N, and channel pitch p in the formula (1)

The relationship between the number of channels, N, and the channel pitch p in the above formula (1) is shown in FIG. 14. Here, as values which can be realized, θ=0.1 deg and $\lambda/NA^2-\alpha=10$ μm and 20 μm were used. The number of the channels C which can be simultaneously put into measurement is preferably as large as possible. When the number of the channels C increases, however, the channel pitch is reduced, making it difficult to produce the chip. Taking the channel pitch suitable for production and the merit of the simultaneous measurement for a larger number of channels into account, the number of channels C is desirably about 6 to 12, and the channel pitch is desirably about 0.6 to 2.0 mm. Besides, the size of the lens array is determined by the lens pitch multiplied by the number of channels; therefore, the smaller this value, the smaller the size of the optical system which can be realized.

Figure 15:
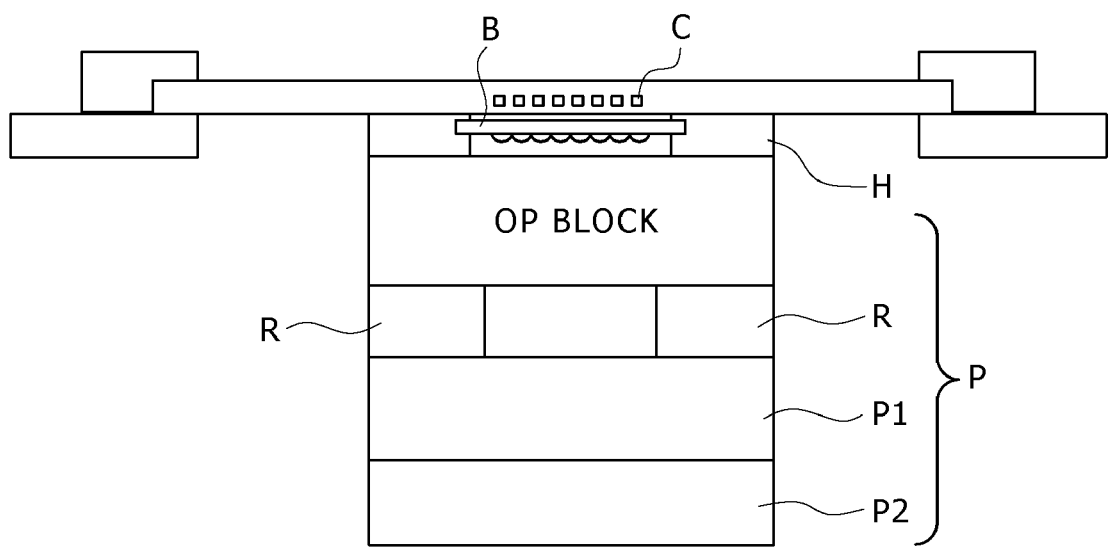
FIG. 15 is a schematic illustration of an example of the configurations of a holder H and a parallelism securing base P, for minimizing the inclination between the chip having channels C and the lens array.

Thus, in order to minimize the inclination between the chip having the channels C and the lens array, a holder H and a parallelism securing base P as shown in FIG. 15 can be used. Examples of the specific configuration of the holder H and the parallelism securing base P include a configuration which has a holder H for obtaining parallelism by making contact with the chip having the channels C, a height adjusting base P2 capable of vertical movements, a rotational adjusting base P1 capable of rotation for adjusting the positions of the channels C, and an elastic body R which is composed of a spring made of a metal or the like or an elastic body of a rubber or the like and which absorbs an angular difference between the holder H and the chip.

Figure 16:
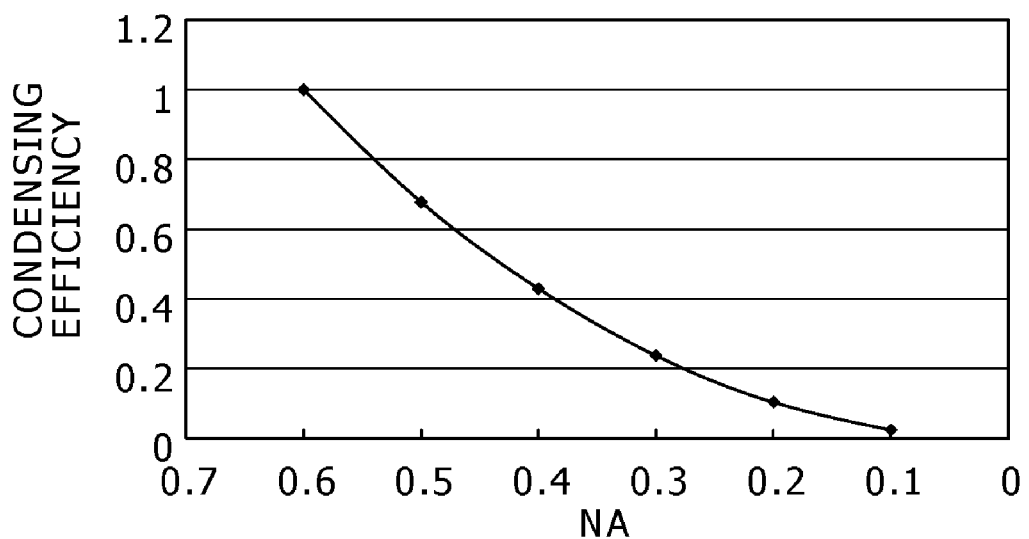
FIG. 16 is a graph substituted for drawing, showing the relationship between the NA of a condenser lens and condensing efficiency, in the case of condensing fluorescent light coming from a channel covered with a cover having a refractive index of 1.5.

In the case where the channels C are irradiated with excitation light and the fluorescent light generated from each of the samples present in the channels C is condensed, the numerical aperture NA of the objective lens used for light condensation is preferably as high as possible, in order to condense the fluorescent light as much as possible. FIG. 16 shows the relationship between the NA of a condenser lens and the condensing efficiency in the case of condensing the fluorescent light coming from the channel C covered with a cover having a refractive index of 1.5. Here, the values of condensing efficiency are normalized by the condensing efficiency at the time when NA=0.6. As seen from FIG. 16, it is desirable for the NA of the condenser lens to be not less than 0.4.

In the case where the fluorescent light from each channel C is condensed by use of a lens array having a lens pitch of 0.6 to 2.0 mm as above-mentioned, examples of the method for producing a lens array with such a lens pitch include a method in which a glass is directly processed by a semiconductor process, and a method in which a molding die is prepared and a molded glass lens is produced. However, neither of the two methods makes it possible to enlarge the sag (see FIG. 13) of the lens. Therefore, it is difficult by such a method to produce a lens having a great numerical aperture. For example, in the case of a double-aspheric lens with a lens diameter of 0.8 mm, a lens thickness of 0.6 mm, a sag of 0.11 mm and a refractive index of the lens material of 1.5, the upper limit of the NA which can be obtained is about 0.6. (It is to be noted here, however, that it may be possible to slightly enhance the NA by using a lens material which has a somewhat higher refractive index.)

Figure 17:
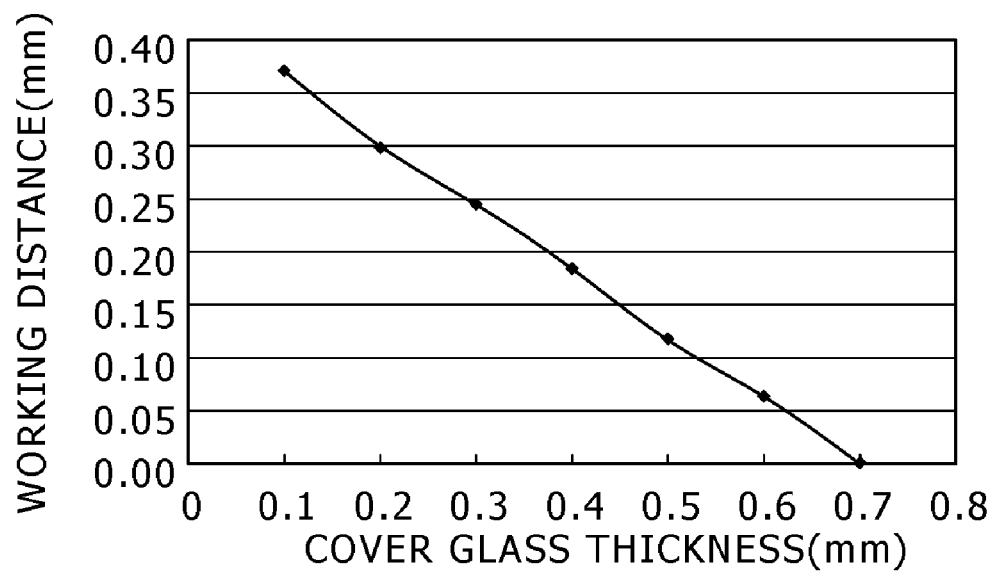
FIG. 17 is a graph substituted for drawing, showing the relationship between cover glass thickness and working distance, in the case where the lens diameter is 0.8 mm and the NA is 0.56.

FIG. 17 shows the relationship between cover glass thickness and working distance in the case where the lens diameter is 0.8 mm and the NA is 0.56. Here, the cover glass is a chip cover layer, with the channels C located at a lowermost portion of the cover layer. If the cover glass thickness is too small, it is difficult to confine samples in the channels C. Besides, since either of the chip and the lens is moved at the time of adjusting the distance therebetween, it is preferable that the working distance is not less than a certain value. Paying attention to ranges of the variables for simultaneously satisfying these two conditions, it is seen from FIG. 17 that when the cover glass thickness is about 0.2 to 0.4 mm, a working distance of 0.15 to 0.3 mm can be secured.

In producing the lens array by arranging lenses in this manner, a space should be present between the adjacent lens areas for a reason on a production basis. In addition, for facilitating the reduction of crosstalk arising from the channels adjacent to the channel in question at the time of measurement, the actual lens diameter is preferably set to be slightly smaller than the lens pitch.

Incidentally, the irradiation with light by use of a beam splitting element B may be applied to one location in one channel C, as in the ninth embodiment shown in FIG. 10 and in the tenth embodiment shown in FIG. 11. Alternatively, however, the irradiation with light by use of a beam splitting element B may also be applied to a plurality of locations in one channel C, as for example in an eleventh embodiment shown in FIG. 18.

(e) Method of Adjusting the Spot Positions in the Case where Light Guide Plate G or Beam Splitting Element B is Used In the case of irradiating a plurality of detection regions 111 with light by use of a light guide plate G or a beam splitting element B, a manufacturing error may be generated as to the pitch of spot positions. In addition, in the case where a plurality of detection regions 111 are provided in a channel C or wells W, a manufacturing error may also be generated as to the pitch of the detection regions 111. In view of this, in the present application, the spot positions can be easily adjusted by the following method.

Figure 19:
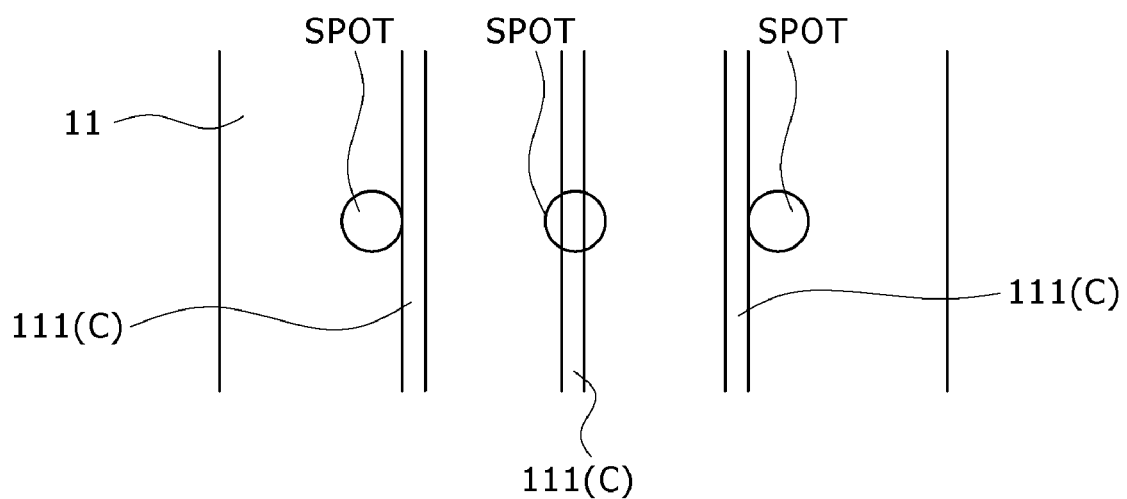
FIG. 19 is a schematic top plan view, as viewed from above the substrate, for illustrating a method of adjusting spot positions, in the case where a light guide plate G or a beam splitting element B is used.
Figure 20:
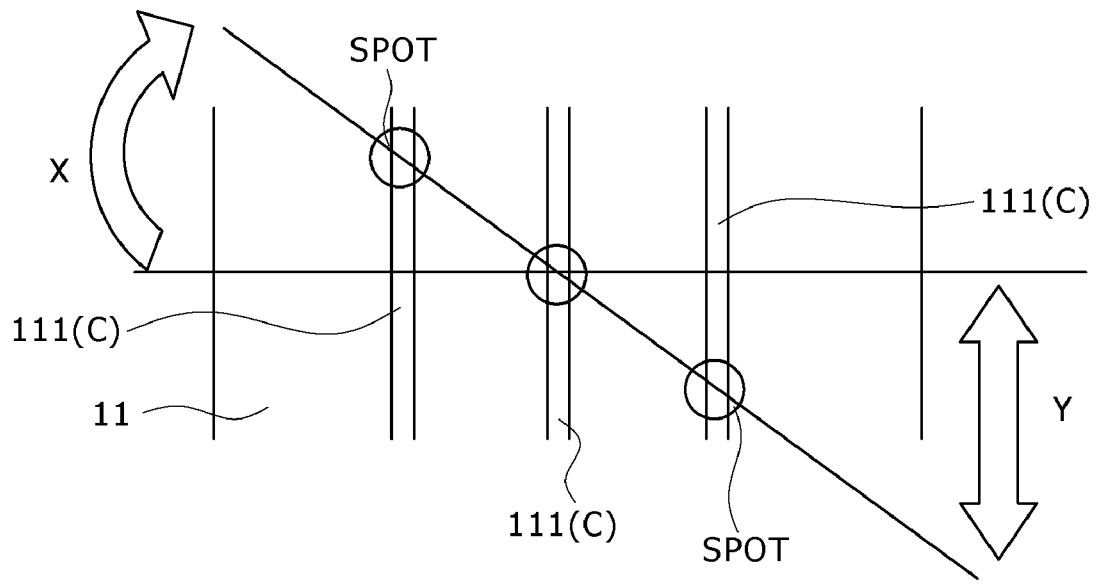
FIG. 20 is a schematic top plan view, as viewed from above the substrate, for illustrating the method of adjusting the spot positions, in the case where the light guide plate G or the beam splitting element B is used.

First, as shown in FIG. 19, the pitch of the spots is preliminarily set to be larger than the pitch of the detection regions 111. Next, as for example shown in FIG. 20, the spot positions are rotationally regulated in the direction of arrow X, whereby it is possible to achieve an adjustment such that the detection regions 111 can be assuredly irradiated with light. In this case, a deviation Y along the flow direction of the channels C is generated between the spot positions. However, this does not matter if the spot pitch is preliminarily so set that the deviation Y will be within an allowable range for measurement.

(4) Light Detection Means 14

The light detection means 14 is a means for detecting the fluorescent light F emitted from the inside of a sample.

In the light detection device 1 according to an embodiment, the specific method for laying out the light detection means 14 is not particularly limited, and the light detection means 14 can be arranged freely, insofar as the fluorescent light F emitted from the inside of each sample can be detected. For instance, as in the first to fourth, seventh, eighth, tenth and eleventh embodiments shown in FIGS. 1 to 4, 7, 8, 10 and 11, a plurality of light detection means 14 can be arranged correspondingly to the detection regions 111. With the plurality of light detection means 14 thus arranged, it is possible to simultaneously detect the fluorescent lights F emitted from the inside of the samples present in the detection regions 111.

In addition, for example, though not shown in the drawings, a configuration may be adopted in which one light detection means 14 is provided for a plurality of detection regions 111 and the light detection means 14 is scanned, whereby the fluorescent lights F emitted from the inside of the samples present in the detection regions 111 can be detected.

Besides, in the light detection device 1 according to an embodiment, the light irradiation means 12 and the light detection means 14 are preferably not arranged in the same direction in relation to the detection regions 111. With the light irradiation means 12 and the light detection means 14 arranged at different positions in relation to the detection regions 111, the light irradiation means 12 and the light detection means 14 can be arranged with a higher degree of freedom.

The detection method applicable to the light detection means 14 in the light detection device 1 according to the present application is not particularly limited, and known light detection methods can be freely selected for use here. Examples of the applicable detection method include a method in which an area image sensor such as photodiodes (PD), charge-coupled device (CCD), complementary metal-oxide semiconductor (CMOS), etc. is used, and a method in which a so-called multi-channel light detection device having a plurality of light detection devices arranged in an array is used.

(5) Condenser Lens 15a, 15b

Figure 18:
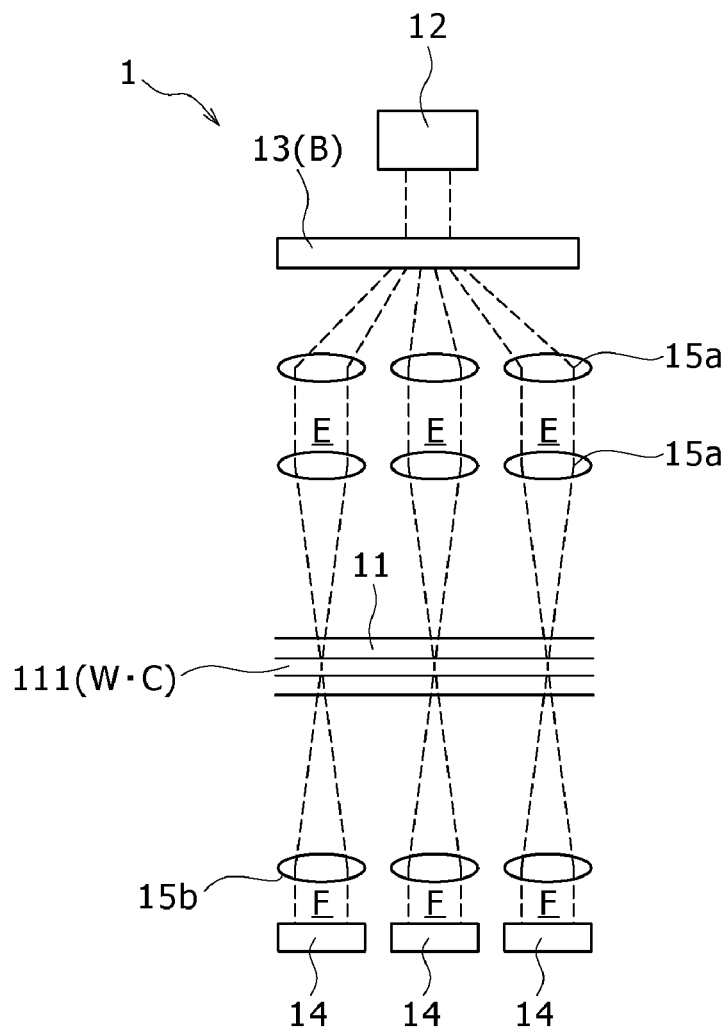
FIG. 18 is a schematic side sectional view, as viewed from a lateral side of a substrate, in an eleventh embodiment of the light detection device according to the application.

In the light detection device 1 according to an embodiment, as in the ninth embodiment shown in FIG. 10 and in the eleventh embodiment shown in FIG. 18, a plurality of excitation condenser lenses 15a may be arranged between the light irradiation means 12 and the detection regions 111 for condensing the light from the light irradiation means 12 onto the detection regions 111. In the light detection device 1 according to embodiments, the excitation condenser lenses 15a are not indispensable, but, where the excitation condenser lenses 15a are provided as in these embodiments, the samples present in the detection regions 111 can be irradiated with light more accurately.

In addition, in the light detection device 1 according to an embodiment, as in the first to fourth, seventh to tenth embodiments shown in FIGS. 1 to 4, 7, 8, 10 and 11, a plurality of light reception condenser lenses 15b may be arranged between the detection regions 111 and the light detection means 14 for condensing the fluorescent lights emitted from the inside of the samples present in the detection regions 111 onto the light detection means 14. In the light detection device 1 according to embodiments, the light reception condenser lenses 15b are not indispensable, but, where the light reception condenser lenses 15b are provided as in these embodiments, signals of the fluorescent lights F and the like can be enhanced more. As a result, an enhanced SN can be realized.

(6) Optical Filter 16a, 16b

Figure 21:
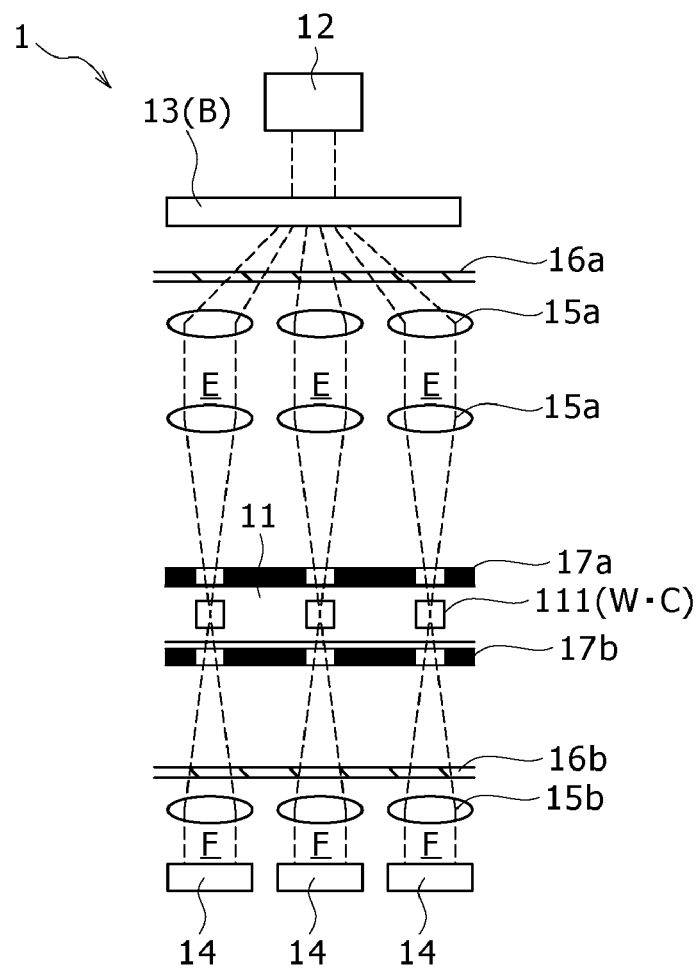
FIG. 21 is a schematic side sectional view, as viewed from a lateral side of a substrate, of a twelfth embodiment of the light detection device.

FIG. 21 is a schematic side sectional view, as viewed from a lateral side of a substrate 11, of a twelfth embodiment of the light detection device 1. In this embodiment, an excitation optical filter 16a is provided between the light irradiation means 12 and the detection regions 111. In the light detection device 1 according to embodiments, the excitation optical filter 16a is not indispensable, but, where the excitation optical filter 16a is provided as in this embodiment, each of the detection regions 111 can be selectively irradiated with excitation light having a desired wavelength.

Besides, in this embodiment, a light reception optical filter 16b is provided between the detection regions 111 and the light detection means 14. In the light detection device 1 according to an embodiment, the light reception optical filter 16b is not indispensable, but, where the light reception optical filter 16b is provided as in this embodiment, light having a desired wavelength can be selectively received from the fluorescent light F emitted from the inside of the sample present in each of the detection regions 111.

(7) Aperture Member 17a, 17b, Partition Wall

In the twelfth embodiment shown in FIG. 21, an aperture member 17a is provided between the light irradiation means 12 and the detection regions 111. In the light detection device 1 according to an embodiment, the aperture member 17a is not indispensable, but, where the aperture member 17a is provided as in this embodiment, radiation of light from the light irradiation means 12 to other detection regions 111 (adjacent detection regions and the like) than the aimed detection region 111 can be obviated. As a result, an enhanced SN can be realized.

Besides, in this embodiment, an aperture member 17b is provided also between the detection regions 111 and the light detection means 14. In the light detection device 1 according to an embodiment, the aperture member 17b also is not indispensable, but, where the aperture member 17b is provided as in this embodiment, crosstalk arising from other detection regions 111 (adjacent detection regions and the like) than the detection region 111 in question can be suppressed. Consequently, an enhanced SN can be obtained.

Incidentally, in the light detection device 1 according to an embodiment, in place of the aperture members 17a and 17b, partition walls may be provided between the lenses, whereby an effect equivalent to the above-mentioned can be produced.

Application of the light detection device 1 according to an embodiment as above-described is not limited to the analysis of properties of substances contained in the samples present in the detection regions 111. For example, when the detection regions 111 are provided in the channels C and this configuration is combined with an electrophoretic method, quantitative analysis of the substances contained in the samples can also be performed.

In addition, for example, when a flow cell is formed by sandwiching a liquid sample between sheath flows, fluorescence intensity or a fluorescent image arising from a substance flowing in the flow cell can be picked up by the light detection means 14. As a structure of such a flow cell, there can be used those structures which have widely been researched, developed and put into practical use as flow cytometry. By performing detection of light from the samples flowing in microchannels C in the above-mentioned manner, microscopic particles such as cells and nucleic acids in the samples can be fractionally collected on the downstream side of the channels, based on the information obtained by the light detection.

Example 1

In Example 1, a light detection device 1 using a lens array as a beam splitting element B functioning as the optical control means 13 was produced. Specifically, a chip having eight channels C was used, and excitation and fluorescent light detection were carried out simultaneously with respect to the eight channels C.

The specifications of the lens array used in Example 1 were a number of lenses of 8, a lens pitch of 0.8 mm, a lens diameter of 0.77 mm, a lens thickness of 0.63 mm, a focal distance of 0.69 mm, a numerical aperture (NA) of 0.55, and a lens material of quartz, with spherical aberration corrected in relation to a cover glass thickness of 0.2 mm. Incidentally, as above-mentioned, the specifications of the lens array are not limited to the specifications used in Example 1. An equivalent effect can be obtained also with a lens pitch of 0.6 to 1.8 mm, a number of lenses of 6 to 12, a cover glass (CG) thickness of 0.2 to 0.6 mm, and an NA of lens at the time of light condensation of 0.4 to 0.65 (an effective NA of lens at the time of excitation of 0.1 to 0.25).

Figure 22:
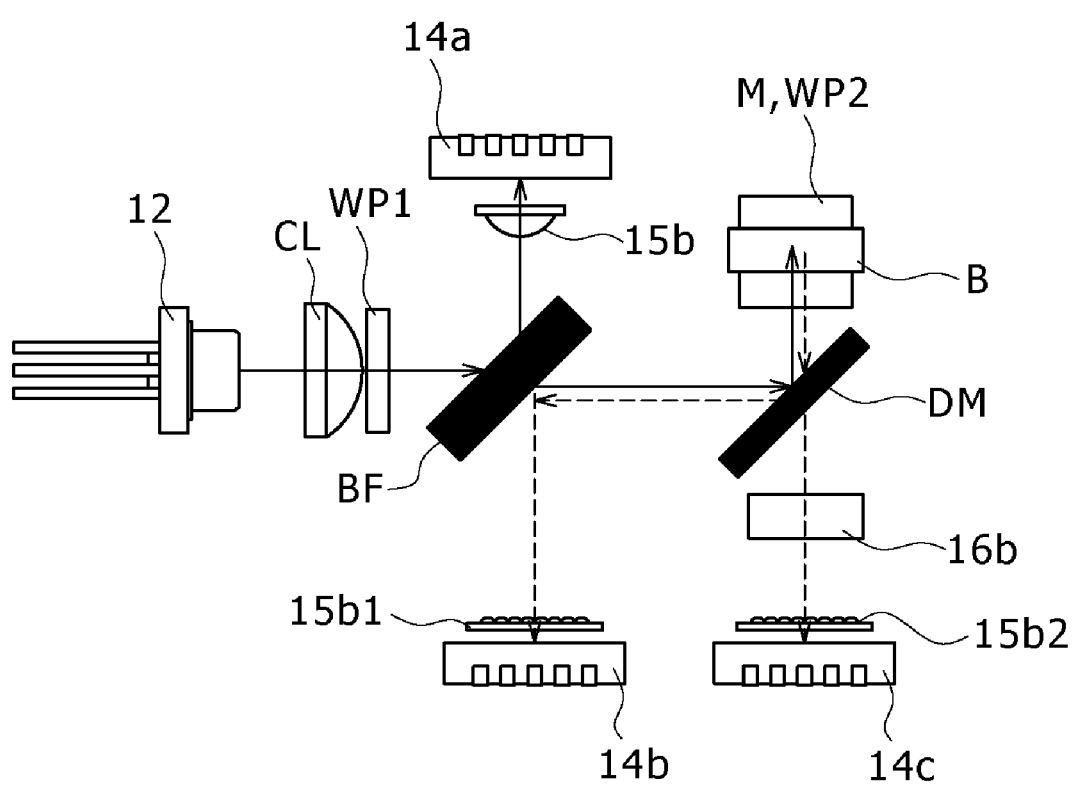
FIG. 22 is a schematic side view showing a specific configuration of the light detection device in Example 1.

The specific configuration of the light detection device 1 produced in Example 1 is as shown in FIG. 22.

Excitation light radiated from a laser diode provided as the light irradiation means 12 is converted into a parallel beam by a collimator lens CL, and its plane of polarization is rotated by a desired angle θ by a half-wave plate WP1. Here, the desired angle θ is in the relationship of the following formula (3) with the quantity I1 of light in a polarization direction perpendicular to the paper sheet surface and the quantity I2 of light in a polarization direction parallel to the paper sheet surface.

[Mathematical 3]

$$\tan \theta = I1 \div I2 \quad (3)$$

The excitation light in the polarization direction perpendicular to the paper sheet surface is reflected by a bandpass filter BF, and is condensed by a light reception condenser lens 15b to be incident on a front APC photodetector 14a provided as light detection means 14, where it is converted into an electrical signal, which is used for controlling the quantity of light radiated from the laser diode provided as the light irradiation means 12. On the other hand, the light in the polarization direction parallel to the paper sheet surface is transmitted through the bandpass filter BF, is reflected by a dichroic mirror DM and a raising mirror M, and is processed by a quarter-wave plate WP2 to be circularly polarized light, which is condensed on a channel C (not shown) by a lens array (objective lens) provided as a beam splitting element B functioning as the optical control means 13.

The reflected light from the channel C returns along the same route as the forward path. However, since the reflected light has been processed by the quarter-wave plate WP2 to be the light in the polarization direction perpendicular to the paper sheet surface, it is reflected by the bandpass filter BF, and is condensed by the light reception condenser lens 15b1 (lens array) to be incident on a focus detection photodetector 14b provided as the light detection means 14, where it is converted into an electrical signal, which is used for detecting the position of the channel C (not shown).

In addition, where a fluorescent substance is present at a light irradiation position in the channel C (not shown), light having a wavelength slightly longer than the wavelength of the laser diode provided as the light irradiation means 12 is generated. This light is condensed by the lens array (objective lens) provided as the beam splitting element B functioning as the optical control means 13, to be a substantially parallel beam. The substantially parallel beam is transmitted through the quarter-wave plate WP2, is reflected by the raising mirror M, is transmitted through a light reception filter 16b, and is condensed by a light reception condenser lens 15b2 to be incident on a fluorescent light detection photodetector 14c provided as the light detection means 14, where it is converted into an electrical signal, which is used for measurement of the quantity of fluorescent light generated in the inside of the channel C.

Example 2

In Example 2, the thickness of a holder H is calculated, in the case where the holder H and a parallelism securing base P as shown in FIG. 15 are used for minimizing the inclination between a chip having channels C and a lens array.

Focal depth is $\lambda/NA^2$, where $\lambda$ is the wavelength of light from a light source and NA is the numerical aperture of an objective lens. The thickness (from a lens surface to a chip contact surface) of the holder H is desirably set to be (the working distance of the objective lens)+(the chip cover glass thickness)$\pm \frac{1}{2} \times \lambda/NA^2$.

In Example 2, the effective objective lens numerical aperture NA at the time of irradiation was 0.1 and the light source wavelength $\lambda$ was 640 nm. From these numerical values, the focal depth was calculated to be $640 \times 10^{-6}/0.1^2 = 0.064$ mm. It has been found out, therefore, that the thickness of the holder should be produced to an accuracy of ±0.032 mm (32 μm).

According to the embodiments, the light radiated from the light irradiation means can be optically controlled so that a plurality of detection regions can be irradiated with the light. Therefore, a plurality of detection regions can be assuredly irradiated with light even if the number of the light irradiation means is smaller than the number of the detection regions. As a result, reductions in overall device size and in energy consumption can be realized.

Use of this technology makes it possible to perform analysis or the like with reduced power consumption, in actual scenes (for example, medical sites) in a variety of fields such as medical fields (pathology, tumor immunology, transplantation medicine, genetics, regeneration medicine, chemotherapy, etc.) as well as the fields of drug design, clinical tests, foods, agriculture, engineering, forensic medicine, criminal identification, and so on.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A light detection device comprising, at least:
   a substrate provided with a plurality of detection regions where to perform detection of fluorescent light emitted from the inside of a sample upon irradiation of the sample with light;
   light irradiation means operable to perform the irradiation with light from a lateral side of the substrate;
   optical control means for irradiating the detection regions with the light radiated from the light irradiation means, the optical control means including a plurality of lenses arranged on an optical path of the light radiated from the light irradiation means so as to reflect the optical path causing the light to radiate directly to the each of the corresponding detection regions; and
   light detection means operable to detect the fluorescent light.

2. The light detection device according to claim 1, wherein the plurality of lenses are replaced with a plurality of mirrors arranged, in the manner of corresponding to the detection regions, on the optical path of the light radiated from the light irradiation means.

3. The light detection device according to claim 1, wherein the plurality of lenses are replaced with a light guide plate.

4. The light detection device according to claim 3, wherein the light guide plate is provided on an opposite side of the substrate from the light detection means.

5. The light detection device according to claim 1, wherein the plurality of lenses are replaced with a beam splitting element.

6. The light detection device according to claim 5, wherein the beam splitting element is provided on an opposite side of the substrate from the light detection means.

7. The light detection device according to claim 1, wherein the detection regions are provided in a plurality of wells provided on the substrate.

8. The light detection device according to claim 1, wherein the detection regions are provided in a channel provided on the substrate.

9. The light detection device according to claim 1, further comprising a filtering means provided along the optical path operable to select a wavelength of the light radiated on the plurality of detection regions.

10. The light detection device according to claim 1, further comprising a filtering means provided along the optical path operable to select a wavelength of the fluorescent light received in the light detection means from the plurality of detection regions.

* * * * *